(12) United States Patent
Mikkonen et al.

(10) Patent No.: US 10,248,525 B2
(45) Date of Patent: Apr. 2, 2019

(54) INTELLIGENT MEDICAL IMPLANT AND MONITORING SYSTEM

(71) Applicant: BAYER OY, Turku (FI)

(72) Inventors: Joonas Mikkonen, Lempäälä (FI); Tero Jalkanen, Turku (FI); Mikko Virtanen, Halikko (FI); Taina Tjäder, Piispanristi (FI); Karym El Sayed, Berlin (DE); Arto Pakkalin, Espoo (FI)

(73) Assignee: Bayer Oy, Turku (FI)

( * ) Notice: Subject to any disclaimer, the term of this patent is extended or adjusted under 35 U.S.C. 154(b) by 0 days.

(21) Appl. No.: 15/729,028

(22) Filed: Oct. 10, 2017

(65) Prior Publication Data

US 2018/0101460 A1    Apr. 12, 2018

Related U.S. Application Data

(60) Provisional application No. 62/406,657, filed on Oct. 11, 2016.

(51) Int. Cl.
*G08B 1/08* (2006.01)
*G06F 11/30* (2006.01)
(Continued)

(52) U.S. Cl.
CPC ...... *G06F 11/3013* (2013.01); *A61B 1/00016* (2013.01); *A61B 1/00066* (2013.01); *A61B 1/00087* (2013.01); *A61B 1/05* (2013.01); *A61B 1/0676* (2013.01); *A61B 17/3468* (2013.01); *A61B 34/20* (2016.02); *A61B 90/98* (2016.02); *A61F 2/82* (2013.01); *A61F 6/20* (2013.01); *A61M 37/0069* (2013.01); *G06F 11/3058* (2013.01); *A61B 2034/2051* (2016.02); *A61F 2250/0002* (2013.01); *A61M 2205/3523* (2013.01); *G06F 17/30312* (2013.01); *H04L 67/1097* (2013.01)

(58) Field of Classification Search
CPC ............ G06F 11/3013; G06F 11/3058; G06F 17/30312; A61B 34/20; A61B 90/98; A61B 1/00016; A61B 1/00087; A61B 1/00066; A61B 1/05; A61B 1/0676; A61B 17/3468; A61B 2034/2051; A61F 2/82; A61F 6/20; A61F 2250/0002; A61M 6/20; A61M 2205/3523; G04L 67/1097
USPC ................................................... 340/539.12
See application file for complete search history.

(56) References Cited

U.S. PATENT DOCUMENTS

| | | | | |
|---|---|---|---|---|
| 5,722,999 A | * | 3/1998 | Snell ................... | A61N 1/37235 607/32 |
| 5,746,697 A | * | 5/1998 | Swedlow ........... | A61B 5/14551 600/323 |

(Continued)

FOREIGN PATENT DOCUMENTS

| | | |
|---|---|---|
| CN | 201993758 U | 9/2011 |
| CN | 202069746 U | 12/2011 |

*Primary Examiner* — Zhen Y Wu
(74) *Attorney, Agent, or Firm* — Nixon & Vanderhye P.C.

(57) ABSTRACT

An intelligent medical implant and monitoring system includes an implant with a communication device, an inserter for inserting the implant, a reader that operates to broadcast a signal specific to the particular communication device that causes the communication device to respond with a unique identifier, and an external database for storing and providing access to information keyed to the unique identifier of the communication device.

30 Claims, 3 Drawing Sheets

(51) Int. Cl.

| | | |
|---|---|---|
| A61F 6/20 | (2006.01) | |
| A61M 37/00 | (2006.01) | |
| A61B 1/05 | (2006.01) | |
| A61B 1/06 | (2006.01) | |
| A61B 1/00 | (2006.01) | |
| A61B 17/34 | (2006.01) | |
| A61B 90/98 | (2016.01) | |
| A61B 34/20 | (2016.01) | |
| A61F 2/82 | (2013.01) | |
| G06F 17/30 | (2006.01) | |
| H04L 29/08 | (2006.01) | |

(56) References Cited

U.S. PATENT DOCUMENTS

| | | | | |
|---|---|---|---|---|
| 5,924,979 A | * | 7/1999 | Swedlow | A61B 5/14551 600/300 |
| 6,200,265 B1 | * | 3/2001 | Walsh | A61B 5/0031 128/903 |
| 6,480,476 B1 | * | 11/2002 | Willars | H04B 1/1615 370/311 |
| 7,899,401 B2 | * | 3/2011 | Tanaka | H04B 17/345 340/10.1 |
| 7,999,655 B2 | * | 8/2011 | Yoshikawa | B60R 25/04 340/5.72 |
| 8,172,766 B1 | * | 5/2012 | Kayyali | A61B 5/02055 600/534 |
| 8,428,528 B2 | * | 4/2013 | Sutton | H04B 1/40 340/10.1 |
| 9,445,051 B1 | * | 9/2016 | Muthsandra Kantharaju | H04N 7/15 |
| 2002/0123672 A1 | * | 9/2002 | Christophersom | A61N 1/37282 600/300 |
| 2003/0171791 A1 | * | 9/2003 | KenKnight | A61N 1/36514 607/60 |
| 2003/0229383 A1 | * | 12/2003 | Whitehurst | A61N 1/372 607/60 |
| 2004/0006492 A1 | * | 1/2004 | Watanabe | A61B 5/0002 705/2 |
| 2004/0113771 A1 | * | 6/2004 | Ozaki | A61B 5/0002 340/539.12 |
| 2005/0247319 A1 | | 11/2005 | Berger | |
| 2007/0279286 A1 | * | 12/2007 | Coutts | H01Q 9/0407 343/700 MS |
| 2008/0004904 A1 | * | 1/2008 | Tran | A61B 5/0006 705/2 |
| 2008/0161660 A1 | * | 7/2008 | Arneson | A61B 1/00016 600/302 |
| 2008/0167531 A1 | * | 7/2008 | McDermott | A61B 5/0031 600/300 |
| 2008/0232405 A1 | * | 9/2008 | Gallo | H04L 47/10 370/498 |
| 2009/0216100 A1 | * | 8/2009 | Ebner | A61B 5/0002 600/347 |
| 2009/0264964 A1 | * | 10/2009 | Abrahamson | A61N 1/37252 607/60 |
| 2010/0315225 A1 | * | 12/2010 | Teague | A61B 5/0024 340/539.12 |
| 2012/0182917 A1 | * | 7/2012 | Edlund | A61N 1/37276 370/311 |
| 2012/0215286 A1 | * | 8/2012 | Rahman | A61N 1/37276 607/60 |
| 2012/0271902 A1 | * | 10/2012 | Baliga | H04L 43/0811 709/209 |
| 2012/0313760 A1 | * | 12/2012 | Okano | G06F 19/3418 340/10.1 |
| 2013/0109989 A1 | * | 5/2013 | Busse | A61B 5/1102 600/527 |
| 2013/0256412 A1 | * | 10/2013 | Yeh | G06K 7/10316 235/439 |
| 2014/0084060 A1 | * | 3/2014 | Jain | G06Q 10/087 235/385 |
| 2014/0141759 A1 | * | 5/2014 | Roper | H04W 4/023 455/418 |
| 2015/0005650 A1 | * | 1/2015 | Banet | A61B 5/0006 600/509 |
| 2015/0265843 A1 | * | 9/2015 | Wu | A61N 1/37252 607/60 |
| 2016/0058324 A1 | * | 3/2016 | Cao | A61B 5/7282 600/302 |
| 2016/0157868 A1 | * | 6/2016 | Tillman | A61F 2/966 606/194 |
| 2016/0183776 A1 | * | 6/2016 | Yamanaka | A61C 1/08 433/29 |
| 2016/0249900 A1 | * | 9/2016 | Aoki | A61M 25/0155 606/130 |
| 2016/0250486 A1 | * | 9/2016 | Yoder | A61N 1/37217 340/870.07 |
| 2016/0306929 A1 | * | 10/2016 | Butka | G06Q 10/1095 |

\* cited by examiner

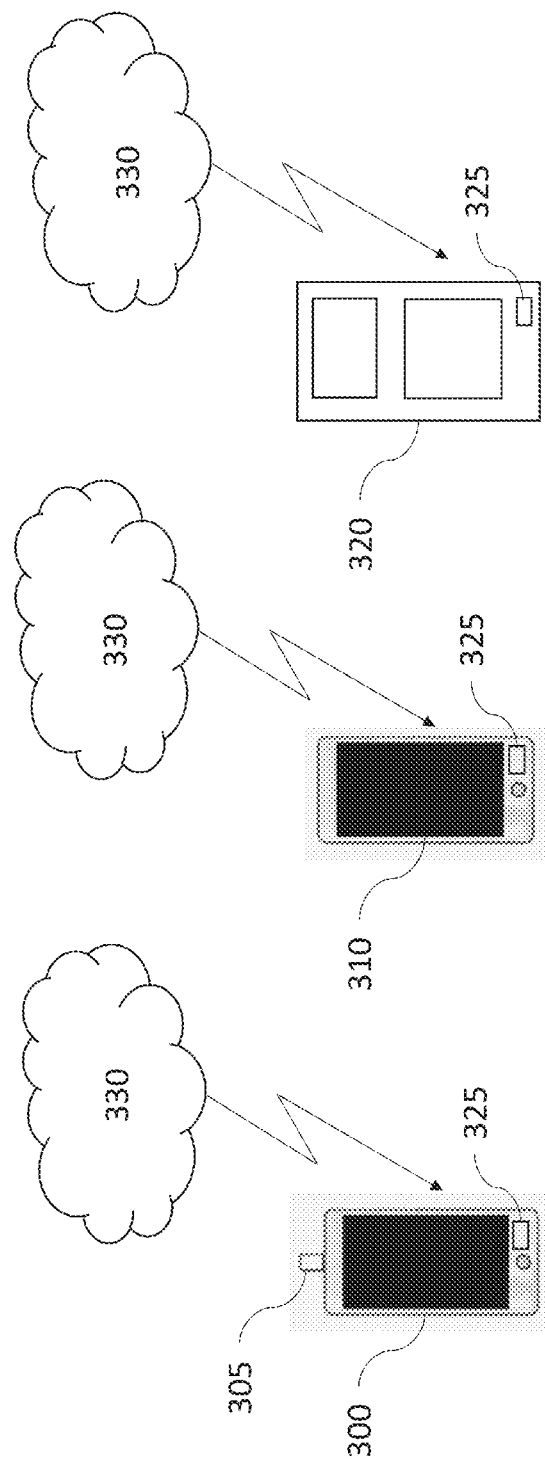

INTELLIGENT MEDICAL IMPLANT AND MONITORING SYSTEM

This application claims the benefit of U.S. Provisional Application No. 62/406,657 filed 11 Oct. 2016, the entire contents of which is hereby incorporated by reference.

FIELD

The disclosed exemplary embodiments relate to a medical implant with a communication device and a system for inserting, communicating with, and monitoring the location of the medical implant after insertion.

BACKGROUND

Various types of medical implants are currently available for supporting biological structures, delivering medication, causing certain reactions in the body, or monitoring body functions, for example, stents, subcutaneous drug delivery systems, fallopian tube inserts, intrauterine drug delivery systems (IUS), and intrauterine devices (IUDs). In the present description, the term "implant" is thus, for sake of clarity and conciseness, used to encompass devices that are implanted in a surgical procedure (such as stents), devices that are implanted using a needle (such as subcutaneous implants) as well as devices that are inserted to a body cavity using an inserter (such as intrauterine system).

An inserter may be used to properly position the medical implant within the body. The inserter may generally include a handle and an insertion tube connected to the handle with a mechanism for grasping and manipulating the medical implant while it is being inserted into the body. When inserting an IUS or IUD, a sound, or alternately, an endometrial aspirator, may be used to measure the direction and length of the cervical canal and uterus. The inserter is then positioned in the body at a distance based on the measurement and the IUS or IUD is inserted.

After being placed in the body, a medical implant is generally inconspicuous and not externally visible, and a patient may have no further indication of the presence of the medical implant, making it difficult for the patient to remember the existence of the medical implant, and making the medical implant difficult to later identify as to type or function. Furthermore, the measurement and insertion operations are performed using tactile feedback without any ability to view the operations as they occur inside the body. Still further, after placement, ultrasound and other imaging techniques requiring expensive and non-portable equipment are used to monitor the location of medical implant devices to make sure they remain in the proper position.

Recent advances in sensor, electronics, and power source miniaturization have resulted in a proliferation of devices with communication facilities and with monitoring capabilities. In addition, the ability to write applications for mobile devices has resulted in the ability to add monitoring facilities to computing or communication devices already being carried by individuals, for example, smart phones, tablet computers, or laptops. It would be useful to be able to take advantage of these technological advances for identifying a specific medical implant among other similar medical implants with a quick and reliable technique. It would also be useful to be able to take advantage of these technological advances when inserting, and subsequently locating medical implants and for providing a wider scope of available information related to medical implants when in situ.

SUMMARY

As described herein, the exemplary embodiments overcome one or more of the above or other disadvantages known in the art.

The disclosed embodiments are directed to an intelligent medical implant and a monitoring system that includes an implant with a communication device, an inserter for inserting the implant, a reader that operates to broadcast a signal specific to a particular communication device that causes the communication device to respond with a unique identifier, and an external database for storing and providing access to information keyed to the unique identifier of the communication device.

The communication device may include a semiconductor chip and an antenna for effecting communication with the reader.

The semiconductor chip may include a memory for storing the identifier.

The communication device may be a passive radio frequency identification tag configured to respond with the unique identifier when exposed to a radio frequency signal from the reader.

The communication device may utilize communication protocols in compliance with international data security regulations and guidelines.

One or more communication devices may be located at one or more positions embedded within or mounted on the implant.

The communication device may be encapsulated with a covering or coating to protect the communication device from the environment when inserted in the body.

The inserter may include a handle coupled to an insertion tube and a mechanism for handling and placing the implant inside the body at a designated location.

The inserter may further include a camera and a light attached to an end of the insertion tube for providing visibility into the body for accurate implant placement.

The inserter may include circuitry for communicating with the communication device and storing the unique identifier in the communication device during an insertion process.

The inserter may include a wireless interface for communicating with one or more display devices.

The inserter may also utilize the wireless interface to communicate with the reader for uploading the unique identifier to the external database.

The reader may generally operate to broadcast a signal specific to a particular communication device, that when recognized by that particular communication device, causes the communication device to respond with an identifier.

The reader may generally utilize communication protocols in compliance with international data security regulations and guidelines similar to those utilized by the communication device.

The reader may be capable of determining a location and orientation of the implant by measuring the signal strength from a plurality of communication devices incorporated with the implant.

The reader may be implemented using a pre-existing device by plugging a module into an external access port of the pre-existing device.

The external database may be implemented as a cloud based system.

The external database may store and provide access to information keyed to the unique identifier assigned to the communication device.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

FIGS. 3A-3C illustrate exemplary readers according to the disclosed embodiments; and

DETAILED DESCRIPTION

Figures 1A, 1B, 1C:
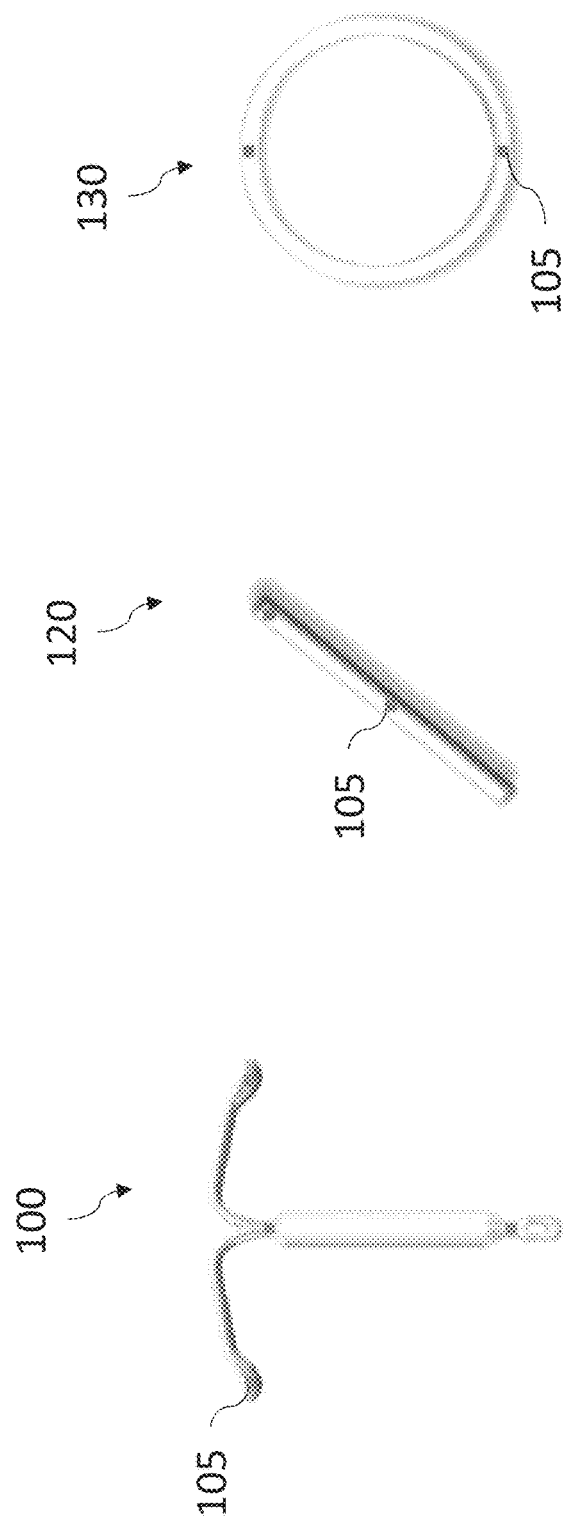
FIGS. 1A-1C display various examples of medical implants according to the disclosed embodiments.

While the medical implants of the disclosed embodiments are described in terms of an IUD or IUS, it should be understood that the medical implant, also referred to as an "implant," may be any medical implant, including a stent, a subcutaneous drug delivery system, a fallopian tube insert, vaginal ring or any suitable implantable device.

An exemplary implant may include at least one communication device which may include a semiconductor, a semiconductor die mounted on a carrier, a printed circuit, or other electronic device capable of effecting the communication facilities described herein. In some embodiments, the communication device may include a semiconductor chip and an antenna. The semiconductor chip may include a memory for storing a program, and one or more of a unique ID, a batch or lot number, and a production date. In one or more embodiments, the communication device may be limited to storing data only once to prevent tampering with any stored data. The communication device may be programmed during manufacturing or at the time of insertion. The semiconductor chip may also include processing circuitry for operating the program. In at least one embodiment, the communication device may be a passive radio frequency identification (RFID) tag and may respond with an identifier or other information when exposed to a radio frequency signal. In some embodiments, the communication device may only store and respond with a unique identifier. The communication device may be capable of utilizing signaling techniques and frequencies that are effective in transmitting and receiving signals through the human body between the communication device and a reader. The communication device may also utilize communication protocols in compliance with international data security regulations and guidelines.

The communication device may be placed at one or more positions or locations embedded within or mounted on the implant. In various embodiments, the communication device may be small enough to fit inside the implant. For example, the communication device may have dimensions of less than 0.2 mm by 0.3 mm and in some embodiments may have dimensions of less than or equal to 0.1 mm by 0.1 mm. In at least one exemplary embodiment, the communication device may be encapsulated with a covering or coating to protect the communication device from the environment when inserted in the body.

An inserter for use during an implant insertion procedure may include a handle coupled to an insertion tube and a mechanism for handling and placing the implant inside the body at a designated location. The inserter may further include a camera and a light attached to an end of the insertion tube. The light may include one or more LED, compact fluorescent, electrochemical, or be any other suitable light source. Power may be provided for the camera and light by an on-board power source, for example one or more batteries, and the camera and light may be activated by the mechanism for handling and placing the implant inside the body at a designated location. The inserter may also include a wireless interface for communicating with one or more display devices, for example, a monitor, a phone with video capability, or a head mounted display, including a virtual reality headset. The camera, light, wireless interface and display device may be activated during implant insertion, providing visibility into the body for a more accurate implant placement. In some embodiments, the inserter may also include a flange for limiting travel of the insertion tube within the body. A light may optionally be incorporated into the flange in order to provide visibility during implant placement. The inserter may also include circuitry for communicating with the communication device and storing a unique identifier or other information in the communication device during the insertion process. The inserter may also utilize the wireless interface to communicate with a reader for uploading the unique identifier and storing additional information in the external database described below.

An exemplary reader according to the disclosed embodiments may be implemented as a portable device, for example, a smart phone, tablet computer, or laptop and may be used by a patient or healthcare professional. The reader may generally operate to broadcast a signal specific to a particular communication device, that when recognized by that particular communication device, causes the communication device to respond with an identifier. The reader may communicate with the device using various techniques, for example the communication device may implement a protocol that only provides a response when the reader sends a code specific to the particular communication device. The reader may generally utilize communication protocols in compliance with international data security regulations and guidelines similar to those utilized by the communication device.

In addition to communicating with the communication device within the implant, the reader may be capable of determining a location and orientation of the implant, for example by measuring the signal strength from a plurality of communication devices incorporated with the implant. Other techniques may also be used, such as gyroscope and acceleration sensor technologies. The location information may be used by the patient or healthcare professional as a position check to ensure that the implant has not shifted or otherwise remains in the proper position.

The reader may be a device operating one or more of an Android, IOS, or other portable device operating system. In some embodiments, the reader may be implemented using a pre-existing device by plugging a module into an external access port, for example, a Lightning, USB, or charging port of the reader. Another exemplary reader may be implemented using a pre-existing device with an installed mobile application. In addition, a reader may be implemented as a dedicated device with limited additional capabilities. Each reader implementation may also include a further communication interface for communicating with an external database for storing and utilizing patient data associated with the unique implant identifier. While the readers are generally described as being portable devices, it should be understood that the readers are not so limited and may also be implemented using one or more desktop or other stationary computing devices.

The external database may be implemented as a cloud based system, a dedicated server, a database cluster or any suitable combination of hardware and software services. Communication with the external database may be implemented utilizing secure communication protocols in compliance with international data security regulations and guidelines, as described above.

The external database may store and provide access to different information keyed to the unique identifier assigned to the communication device, for example, product name of the implant, manufacturer name and batch number, date and time of placement, effective and safe usage time remaining left for the implant, and general information about the patient. This information may be accessible by an authorized user of any of the implementations of the reader, and may be used to calculate reminders for the next visit to a health care professional, reminders as to the replacement schedule for the implant, or any other information that may be helpful to an authorized patient or healthcare professional.

FIGS. 1A-1C show various examples of medical implants 110, 120, 130 according to the disclosed embodiments. Each exemplary implant 100 may include at least one communication device 105 as described above.

Figure 2:
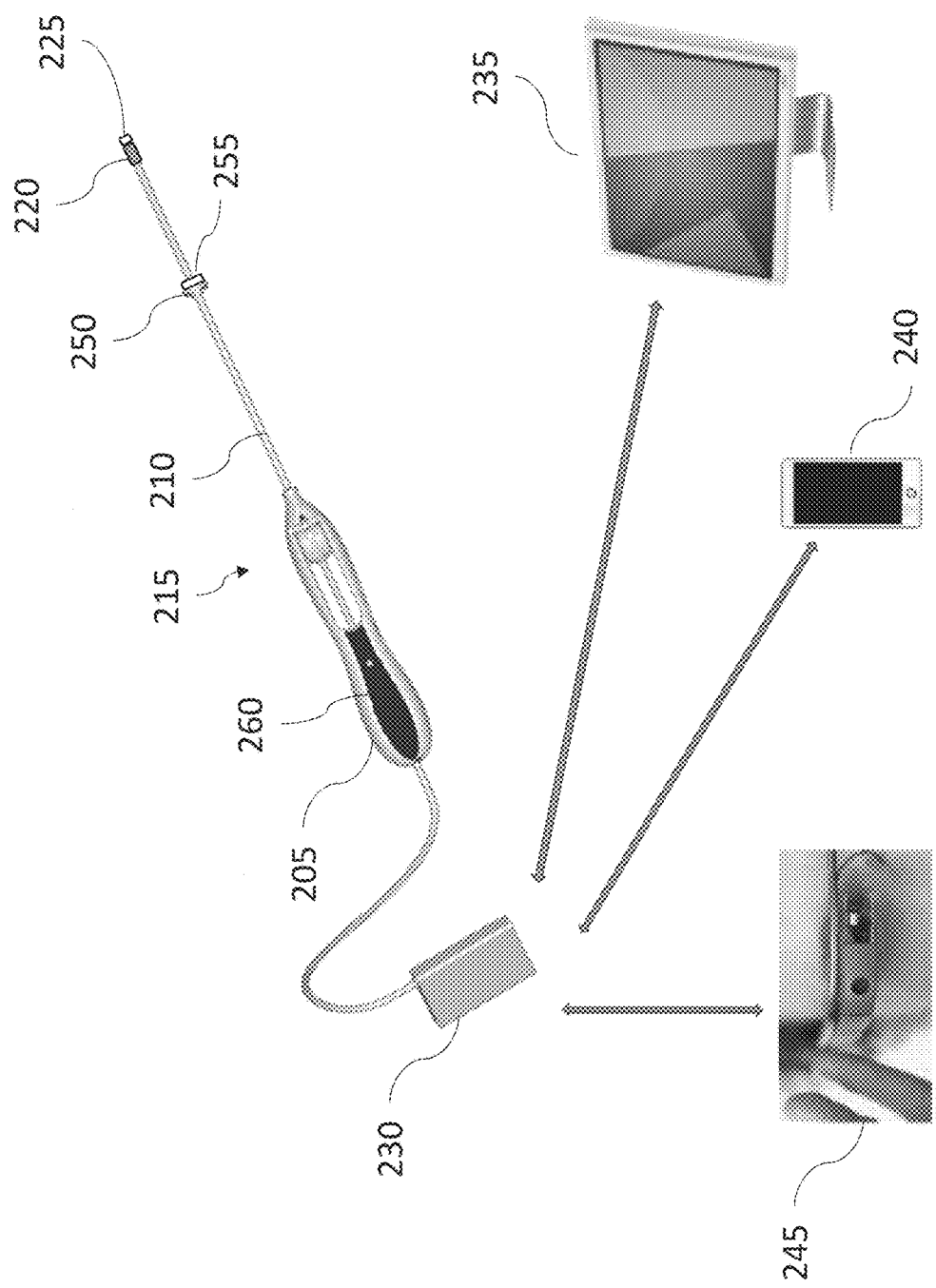
FIG. 2 shows an inserter for use during an implant insertion procedure.

FIG. 2 shows an inserter 200 for use during an implant insertion procedure. The inserter 200 includes a handle 205 coupled to an insertion tube 210 and a mechanism 215 for handling and placing the implant inside the body at a designated location. The camera 220 and light 225 are attached to an end of the insertion tube 210 and the camera and light may be activated by the mechanism 215. The wireless interface 230 communicates with the one or more display devices 235, 240, 245. The light 255 may optionally be incorporated into the flange 250 in order to provide visibility during implant placement. Circuitry 260 communicates with the communication device 105 (FIG. 1) and stores the unique identifier or other information in the communication device 105 during the insertion process.

FIGS. 3A-3C illustrate exemplary readers including reader 300 implemented using a portable device and the module 305 inserted into an external access port. FIG. 3B shows an exemplary reader implemented using a re-existing device with an installed mobile application, and FIG. 3C shows an exemplary reader implemented as a dedicated device with limited additional capabilities. Each reader implementation 310, 320, 330 may also include a further communication interface 325 for communicating with the external database 325 for storing and utilizing patient data associated with the unique implant identifier.

The external database 325 may be implemented as a cloud based system, a dedicated server, a database cluster or any suitable combination of hardware and software services.

The disclosed implants, inserters, monitors, readers, and external database may be implemented together as a system to provide a more accurate insertion of the implant and a wealth of information for both the patient and the healthcare provider regarding the implant. By tying the unique identifier to information stored in the external database, the information is easily and securely accessible to the patient and the healthcare professional.

Various modifications and adaptations may become apparent to those skilled in the relevant arts in view of the foregoing description, when read in conjunction with the accompanying drawings. However, all such and similar modifications of the teachings of the disclosed embodiments will still fall within the scope of the disclosed embodiments.

Various features of the different embodiments described herein are interchangeable, one with the other. The various described features, as well as any known equivalents can be mixed and matched to construct additional embodiments and techniques in accordance with the principles of this disclosure.

Furthermore, some of the features of the exemplary embodiments could be used to advantage without the corresponding use of other features. As such, the foregoing description should be considered as merely illustrative of the principles of the disclosed embodiments and not in limitation thereof.

The invention claimed is:

1. An intelligent medical implant and monitoring system comprising:
   an implant with a communication device;
   an inserter for inserting the implant;
   a reader that operates to broadcast a signal specific to the communication device causing the communication device to respond with a unique identifier; and
   an external database for storing and providing access to information keyed to the unique identifier from the communication device;
   wherein the inserter comprises circuitry for communicating with the communication device and storing the unique identifier in the communication device during an insertion process.

2. The intelligent medical implant and monitoring system of claim 1, wherein the communication device comprises a semiconductor chip and an antenna for effecting communication with the reader.

3. The intelligent medical implant and monitoring system of claim 1, wherein the semiconductor chip comprises a memory for storing the unique identifier.

4. The intelligent medical implant and monitoring system of claim 1, wherein the communication device comprises a passive radio frequency identification tag configured to respond with the unique identifier when exposed to a radio frequency signal from the reader.

5. The intelligent medical implant and monitoring system of claim 1, wherein the communication device is configured to utilize communication protocols in compliance with international data security regulations and guidelines.

6. The intelligent medical implant and monitoring system of claim 1, wherein one or more communication devices are located at one or more positions embedded within or mounted on the implant.

7. The intelligent medical implant and monitoring system of claim 1, wherein the communication device is encapsulated with a covering or coating to protect the communication device from an environment when inserted in a body.

8. The intelligent medical implant and monitoring system of claim 1, wherein the inserter comprises a handle coupled to an insertion tube and a mechanism for handling and placing the implant inside a body at a designated location.

9. The intelligent medical implant and monitoring system of claim 1, wherein the inserter comprises a wireless interface for communicating with one or more display devices.

10. The intelligent medical implant and monitoring system of claim 1, wherein the inserter comprises a camera and a light attached to an end of the insertion tube for providing visibility into a body for accurate implant placement.

11. The intelligent medical implant and monitoring system of claim 1, wherein the reader is configured to broadcast a signal specific to a particular communication device, that when recognized by that particular communication device, causes the communication device to respond with a unique identifier specific to the particular communication device.

12. The intelligent medical implant and monitoring system of claim 1, wherein the reader is configured to determine a location and orientation of the implant by measuring a signal strength from a plurality of communication devices incorporated with the implant.

13. The intelligent medical implant and monitoring system of claim 1, wherein the reader comprises a module inserted into an external access port of a pre-existing device.

14. The intelligent medical implant and monitoring system of claim 1, wherein the external database comprises a cloud based database system.

15. The intelligent medical implant and monitoring system of claim 1, wherein the external database is configured to store and provide access to information keyed to the unique identifier assigned to the communication device.

16. An intelligent medical implant and monitoring system comprising:
    an implant with a communication device;
    an inserter for inserting the implant;
    a reader that operates to broadcast a signal specific to the communication device causing the communication device to respond with a unique identifier; and
    an external database for storing and providing access to information keyed to the unique identifier from the communication device;
    wherein the inserter comprises a wireless interface for communicating with one or more display devices; and
    wherein the inserter is configured to utilize the wireless interface to communicate with the reader for uploading the unique identifier to the external database.

17. The intelligent medical implant and monitoring system of claim 16, wherein the communication device comprises a semiconductor chip and an antenna for effecting communication with the reader.

18. The intelligent medical implant and monitoring system of claim 16, wherein the semiconductor chip comprises a memory for storing the unique identifier.

19. The intelligent medical implant and monitoring system of claim 16, wherein the communication device comprises a passive radio frequency identification tag configured to respond with the unique identifier when exposed to a radio frequency signal from the reader.

20. The intelligent medical implant and monitoring system of claim 16, wherein the communication device is configured to utilize communication protocols in compliance with international data security regulations and guidelines.

21. The intelligent medical implant and monitoring system of claim 16, wherein one or more communication devices are located at one or more positions embedded within or mounted on the implant.

22. The intelligent medical implant and monitoring system of claim 16, wherein the communication device is encapsulated with a covering or coating to protect the communication device from an environment when inserted in a body.

23. The intelligent medical implant and monitoring system of claim 16, wherein the inserter comprises a handle coupled to an insertion tube and a mechanism for handling and placing the implant inside a body at a designated location.

24. The intelligent medical implant and monitoring system of claim 16, wherein the inserter comprises a wireless interface for communicating with one or more display devices.

25. The intelligent medical implant and monitoring system of claim 16, wherein the inserter comprises a camera and a light attached to an end of the insertion tube for providing visibility into a body for accurate implant placement.

26. The intelligent medical implant and monitoring system of claim 16, wherein the reader is configured to broadcast a signal specific to a particular communication device, that when recognized by that particular communication device, causes the communication device to respond with a unique identifier specific to the particular communication device.

27. The intelligent medical implant and monitoring system of claim 16, wherein the reader is configured to determine a location and orientation of the implant by measuring a signal strength from a plurality of communication devices incorporated with the implant.

28. The intelligent medical implant and monitoring system of claim 16, wherein the reader comprises a module inserted into an external access port of a pre-existing device.

29. The intelligent medical implant and monitoring system of claim 16, wherein the external database comprises a cloud based database system.

30. The intelligent medical implant and monitoring system of claim 16, wherein the external database is configured to store and provide access to information keyed to the unique identifier assigned to the communication device.

* * * * *